(12) United States Patent
Rand et al.

(10) Patent No.: US 6,679,254 B1
(45) Date of Patent: Jan. 20, 2004

(54) INHALATION DEVICE

(75) Inventors: Paul Kenneth Rand, Ware (GB); Gregor John McClenan Anderson, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/890,727

(22) PCT Filed: Dec. 8, 1999

(86) PCT No.: PCT/EP99/09615
§ 371 (c)(1),
(2), (4) Date: Oct. 17, 2001

(87) PCT Pub. No.: WO00/45879
PCT Pub. Date: Aug. 10, 2000

(30) Foreign Application Priority Data

Feb. 5, 1999 (GB) ............................................. 9902493

(51) Int. Cl.[7] ........................ A61M 15/00; A61M 16/00; B05D 7/14; B65D 83/06
(52) U.S. Cl. ................................................. 128/203.15
(58) Field of Search ........................... 128/203.21, 266, 128/200.23, 203.15, 203.12, 203.13, 203.14, 203.18

(56) References Cited

U.S. PATENT DOCUMENTS

| | | | |
|---|---|---|---|
| 3,635,219 A | * | 1/1972 | Altounyan et al. ......... 128/266 |
| 4,524,769 A | | 6/1985 | Wetterlin |
| 5,511,540 A | * | 4/1996 | Bryant et al. ........... 128/200.23 |
| 6,065,472 A | * | 5/2000 | Anderson et al. ....... 128/203.21 |

FOREIGN PATENT DOCUMENTS

| | | | |
|---|---|---|---|
| DE | 38 23 35 A | | 1/1990 |
| DE | 19500764 | * | 7/1996 |
| DE | 195 00 764 A | | 7/1996 |
| EP | 0 525 720 A | | 2/1993 |
| WO | WO97 37693 A | | 10/1997 |

\* cited by examiner

Primary Examiner—Henry Bennett
Assistant Examiner—Sabrina Dagostino
(74) Attorney, Agent, or Firm—Robert J. Smith; James P. Riek

(57) ABSTRACT

There is provided a medicament cartridge for use in an inhalation device comprising a carrier having a plurality of medicament retainers in a concentric circular path arrangement. Typically, the carrier is substantially planar. There is also provided an inhalation device comprising a housing having an air inlet, an air outlet, an airway therebetween and a medicament carrier having a plurality of medicament retainers in a concentric circular path arrangement. A mover is provided for moving the medicament carrier relative to the housing so as to bring successive medicament retainers individually into communication with the airway.

39 Claims, 9 Drawing Sheets

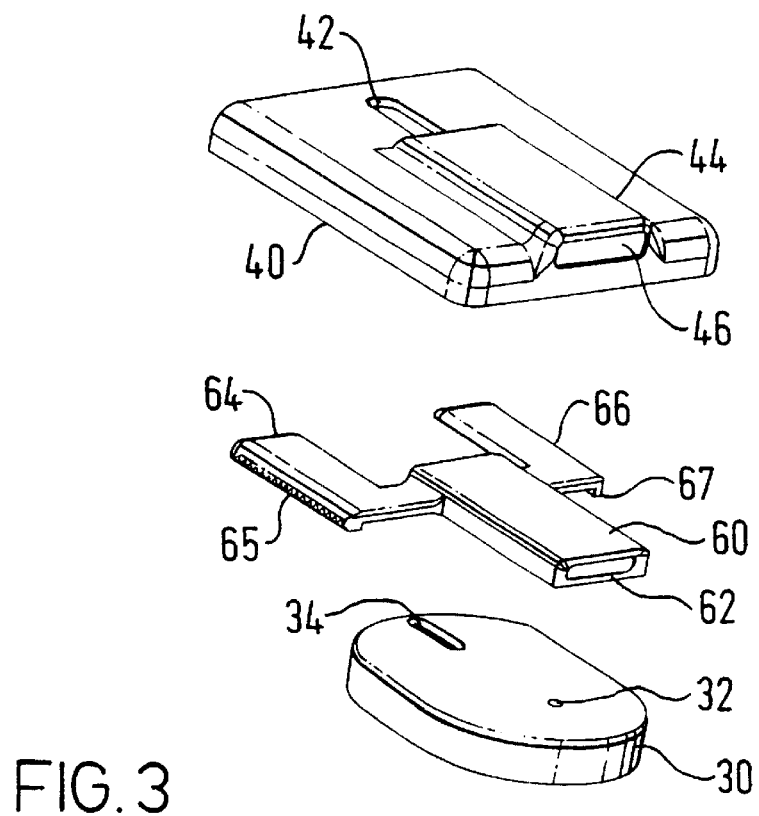
FIG. 3
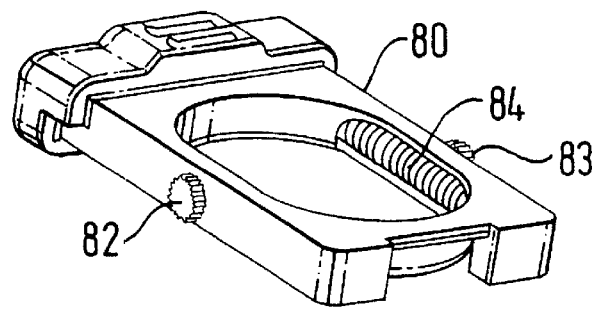
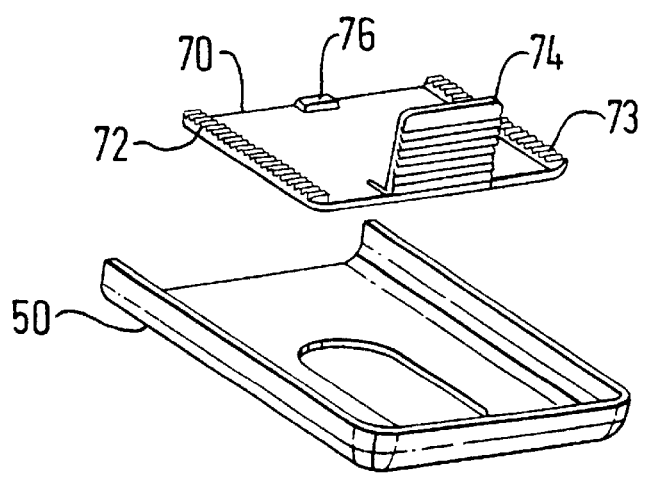

INHALATION DEVICE

The present invention relates to a medicament cartridge for use in an inhalation device for use in the administration of medicament to a patient. The cartridge has a plurality of medicament retainers in a concentric circle arrangement.

The use of inhalation devices in the administration of medicaments, for example in bronchodilation therapy, is well known. Such devices generally comprise a body or housing within which a medicament container is located. A mouthpiece (or nozzle) is typically provided, wherein 'in use' the mouthpiece communicates with the medicament container to allow passage of medicament from the source to the mouthpiece and thence, to the patient.

In a typical dispensing operation the body of the device is held by the patient and the mouthpiece (or nozzle) of the inhalation device is placed in the mouth (or nose) of the patient. The patient inhales, thereby causing transfer of medicament from the medicament container to the interior of the body of the patient.

It is desirable that the inhalation device is able to provide a plurality of doses of medicament. Known devices include metered dose inhalers having an aerosol container comprising sufficient medicament to provide plural individual doses. Also known are dry powder inhalers having a reservoir of dry powder from which individual doses may be delivered.

Other known devices have a medicament carrier having plural individual medicament retainers thereon. One such carrier is shaped in the form of a rigid disc having plural medicament-containing blisters arranged in a circular configuration thereon. Typically, such discs are designed to provide from five to ten doses. Another such carrier has an elongate tape carrier having plural medicament-containing blisters arranged in a line along the length of the tape. The tape is generally retained on a spindle and the tape is progressively unwound from the spindle to allow access to individual blisters. Typically, such tape carriers are designed to provide about forty to sixty doses.

There is continuing interest in the design of medicament cartridges capable of providing very large numbers of individual doses. However, there is also a desire to reduce the size of the device, and hence the cartridge, so that it is readily portable by the patient. It will be appreciated that with the above described known carriers increasing the number of doses will also result in an inevitable and undesirable increase in the required size of disc and tape-winding on the spindle.

The Applicants have now found that the use of a medicament cartridge comprising a carrier having a plurality of individually accessible medicament retainers arranged in a series of concentric circles allows for the provision of large numbers of doses from a single cartridge, whilst enabling the size of the cartridge to be kept at an acceptable level.

According to one aspect of the present invention there is provided a medicament cartridge for use in an inhalation device comprising a carrier having a plurality of medicament retainers in a concentric circular path arrangement.

By concentric circular path arrangement it is meant herein an arrangement comprised of plural circular arrangements of medicament retainers, the circular arrangements being arranged in concentric fashion.

The carrier may be formed from any suitable material including plastic materials. Preferably, the carrier is substantially planar. More preferably, the carrier is substantially rigid. Preferably, the carrier is circular in shape and is rotationally mountable.

In one aspect, the carrier comprises plural concentric rings, each ring comprising a plurality of medicament retainers in a circular path arrangement. Preferably, each ring is lockably engageable with any adjacent ring thereto.

In another aspect the medicament retainers define a spiral ray arrangement.

By spiral ray arrangement it is meant herein an arrangement comprised of plural spiral arrangements of medicament retainers, the spiral arrangements being arranged in concentric fashion.

The medicament retainers are sized and shaped for retention of medicament. Each retainer may for example, be a medicament-retaining pocket. Suitable pocket forms include a cavity (recess) provided in the retainer, a cup having side walls standing proud from the carrier and any composite of these cavity/cup forms. A cover, preferably a hermetically sealing cover, may be provided to the pocket.

The retainer may also for example, be a hole in the retainer. Optionally the hole has freestanding walls provided therearound. The hole may also optionally be provided with a mesh arrangement therein. The mesh may be formed of any suitable materials including plastic materials. Covers, preferably hermetically sealing covers, may be provided to seal the hole.

In one preferred aspect, each medicament retainer comprises a pocket in the carrier. Preferably, a seal is provided to each pocket. In a particularly preferred aspect, the seal comprises a sealing tape arranged along each circular path and each pocket is accessible by progressive removal of the tape from said circular path. In another preferred aspect the seal comprises a rubber seal provided individually to each pocket.

In another preferred aspect, each medicament retainer comprises a hole in the carrier. Each hole may be provided with a mesh for retention of medicament. The medicament may be applied to the mesh by any suitable method including wet and dry printing methods. Suitable wet printing methods include ink jet printing. Suitable dry printing methods include xerographic and electrostatic printing methods.

Preferably, each medicament retainer is sized to retain a single dose of medicament.

Preferably, the medicament cartridge has from 30 to 500, more preferably from 60 to 400, most preferably from 100 to 300, medicament retainers.

When charged for use, medicament is typically present in one or more of the medicament retainers.

According to another aspect of the present invention there is provided a medicament cartridge for use in an inhalation device comprising a carrier having a plurality of medicament doses thereon, wherein said doses are in a concentric circular path arrangement.

The medicament doses may be applied to the carrier by any suitable method including wet and dry printing methods. Suitable wet printing methods include ink jet printing. Suitable dry printing methods include xerographic and electrostatic printing methods.

According to a further aspect of the present invention there is provided an inhalation device comprising
 a housing having an air inlet, an air outlet and an airway therebetween;
 a medicament carrier having a plurality of medicament retainers in a concentric circular path arrangement; and
 a mover for moving the medicament carrier relative to the housing so as to bring successive medicament retainers individually into communication with the airway.

In one aspect the medicament retainers define a spiral ray arrangement.

Preferably, the medicament carrier is a substantially rigid circular disc which is rotatable relative to the housing.

In one aspect, the circumference of the circular disc is provided with teeth and said teeth engage a worm drive for drivable rotation of the disc.

In another aspect, each medicament retainer comprises a pocket in a first face of the disc.

Preferably each medicament retainer has a seal.

In a further aspect, each medicament retainer is individually unsealable.

In one aspect, said seal is provided by a gasket and the interior surfaces of said housing. A first gasket is positioned between the base of the air outlet and the surface of the upper face of the disc, a second gasket is positioned between the circumference of the upper face of the disc and the housing, and a third gasket is positioned between the circumference of the lower face of the disc and the housing.

Preferably, the gasket comprises an organic polymeric material selected from the group consisting of rubber, neoprene, polyester, polyethylene, polycarbonate, polyacetal, polytetrafluroethylene and nylon.

In yet another aspect, the air outlet is in communication with a mouthpiece.

According to a yet further aspect of the present invention there is provided an inhalation device comprising
- a housing having an air inlet, an air outlet and an airway therebetween;
- a medicament carrier having a plurality of medicament retainers in a concentric circular path arrangement, each medicament retainer having a seal;
- an actuator for progressively unsealing each medicament retainer.

In another aspect the medicament retainers define a spiral ray arrangement

Preferably, the device additionally comprises a mover for moving the medicament carrier relative to the housing so as to bring successive medicament retainers individually into communication with the airway.

Preferably, each medicament retainer comprises a pocket.

Preferably, said seal comprises a sealing tape arranged along said concentric circular path and wherein each pocket is serially accessible by peelable removal of the tape. More preferably, an end of said sealing tape connects to said actuator and peelable removal of the sealing tape is achievable by movement of the actuator.

In yet another aspect, the actuator is rotatable relative to the housing such that rotation of the actuator results in coiling of the tape around the actuator. Preferably, the actuator is an axially mounted tapered pole.

In another aspect, the actuator comprises a piercer for piercably unsealing a medicament retainer.

Preferably, the air outlet is provided with a mouthpiece. Herein the term 'mouthpiece' is used in a generic sense to mean an element shaped such as to be insertable into the mouth or nose of a patient for inhalation therethrough.

Preferably, the device is provided with a dose counter, which indicates the number of doses dispensed from or remaining in the container. More preferably, the dose counter comprises an indexing mechanism actuated by a predetermined movement of the medicament container relative to the body.

Preferably, the medicament is in dry-powder form.

According to a still further aspect of the present invention there is provided the use of an inhalation device as described herein for the administration of medicament to a patient.

Preferred embodiments of the present invention will now be described with reference to the accompanying drawings in which:

FIG. 1b is a reverse view of the medicament cartridge of FIG. 1a;

FIG. 3 is an exploded view of an inhalation device incorporating the cassette of FIG. 2;

FIGS. 10b and 10c are side views of the cassette of FIG. 10a;

FIG. 10d is an exploded view of the cassette of FIG. 10a;

Figure 1A:
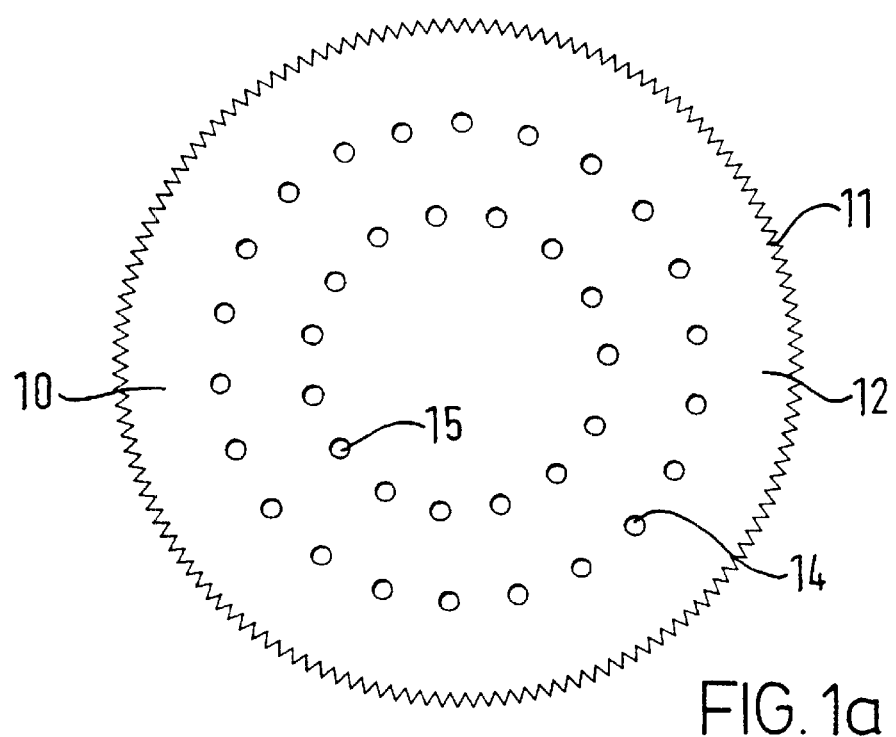
FIG. 1a is a top view of a medicament cartridge in accord with the present invention.
Figure 1B:
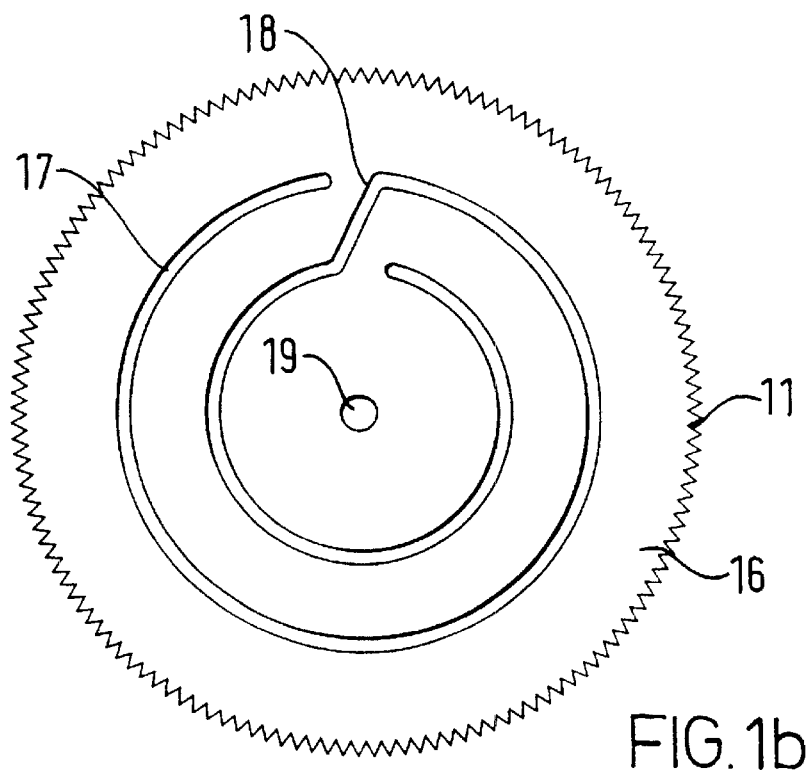

FIGS. 1a and 1b show a medicament cartridge in the form of a rigid disc 10 having teeth 11 on the circumference thereof. The top face 12 of the disc 10 is provided with a plurality of medicament retaining cavities arranged in outer 14 and inner 15 circular arrangements. The outer 14 and inner 15 circles may be seen to be concentric. The reverse face 16 of the disc 10 is provided with a tracking groove 17 and a centrally located peg 19 to enable the disc to be mounted for rotation. The spiral tracking groove 17 may be seen to comprise concentric outer and inner circular grooves (closely mirroring the outer 14 and inner 15 circles of the top face 12) linked by a crossover link 18 which forms a track between the outer and inner circular grooves.

Figure 2:
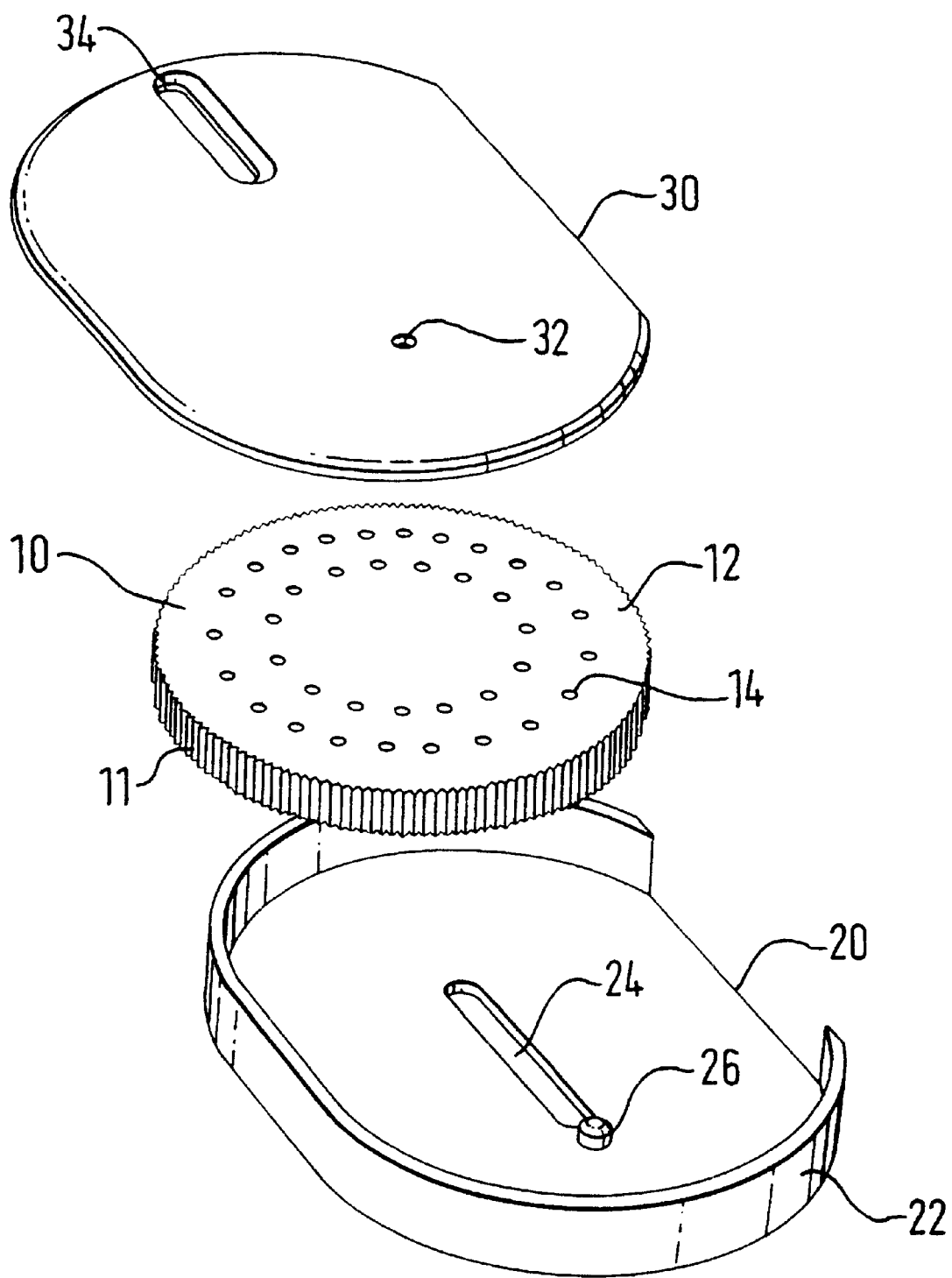
FIG. 2 is an exploded view of a cassette incorporating the medicament cartridge of FIG. 1a and 1b.

FIG. 2. shows an exploded view of a cassette incorporating the medicament cartridge of FIGS. 1a and 1b. The cassette has a bottom cover 20 having peripheral walls 22 extending partially therearound. The bottom cover 20 is provided with a slit 24 for receipt of the peg 19 on the reverse face 16 of the disc 10. The bottom cover 20 is also provided with a tracking pin 26 which is located adjacent to a first end of the slit 24. When the cassette is in assembled form the tracking pin 26 follows the tracking groove 17 on the reverse face 16 of the disc cartridge 10. The top cover 30 of the cassette is provided with an exit hole 32 located to register with successive medicament retaining cavities 14 on the top face 12 of the disc 10. The top cover 30 is also provided with a window 34.

To enable access to successive medicament retainers (doses) in use, it may be understood that the disc 10 will be rotated to bring each successive medicament-retaining cavity 14 into registration with the exit hole 32.

On rotation of the disc 10, the tracking pin 26 follows the tracking groove 17. The pin 26 thus tracks the outer circular groove until the crossover link 18 is reached. This corresponds to the point when all of the medicament retainers of the outer circle 14 have been accessed. At the crossover link 18, the pin 26 crosses onto the inner circular groove thereby causing the disc 10 to be translationally shifted in a direction set by the slit 24 in the bottom cover 20 of the cassette. The medicament retainers of the inner circle 15 may thus be accessed by further rotation of the disc 10. The view through the window 34 provides an indication of the number of doses remaining.

FIG. 3 shows an exploded view of an inhalation device incorporating the cassette of FIG. 2. The device may be seen to comprise an outer casing having first 40 and second 50 interlocking portions.

The first portion 40 is provided with a window 42 which is positioned for registration with the window 34 on the cassette. The first portion 40 of the casing is also seen to have a raised part 44 provided with a generally rectangular opening 46 which is shaped for receipt of mouthpiece 60. The mouthpiece may be seen to have a housing defining an airway 62 which is of generally rectangular shape. The airway 62 is provided with an entrance hole (not shown) which, when the mouthpiece is in the in-use position, communicates with the exit hole 32 in the top cover of the cassette thereby allowing transfer of medicament from a cavity 14 in the disc 10 through to the airway 62. The housing is also provided with two arms 64, 66 having racks 65 thereon.

Figure 4A:
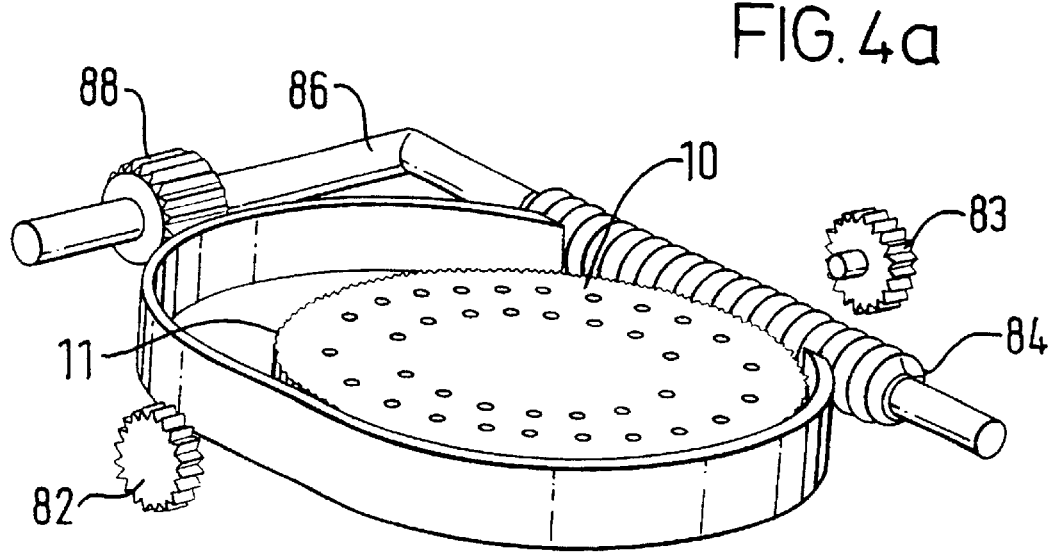
FIG. 4a is a simplified plan view of the drive system of the inhalation device of FIG. 3.

The second portion 50 of the casing is shaped for receipt of mouthpiece slider 70 (shown in more detail in FIG. 4a) which is slidably movable within the second portion 50 of the casing. The mouthpiece slider 70 is provided with racks 72, 73 which communicate via transfer wheels 82, 83 on the main body 80 (shown in more detail in FIG. 4b) with the racks 65, 67 on the arms 64, 66 of the mouthpiece 60. It may thus be seen that slidable movement of the mouthpiece slider 70 enables the mouthpiece 60 to be moved from a storage position within the casing to an in-use position in which it protrudes from the casing. The mouthpiece slider 70 is also provided with a hinged door 74 which may be seen to be movable from a closed position when the mouthpiece 60 is in the storage position to an open position as the mouthpiece 60 is moved to the in-use position.

Figure 4B:
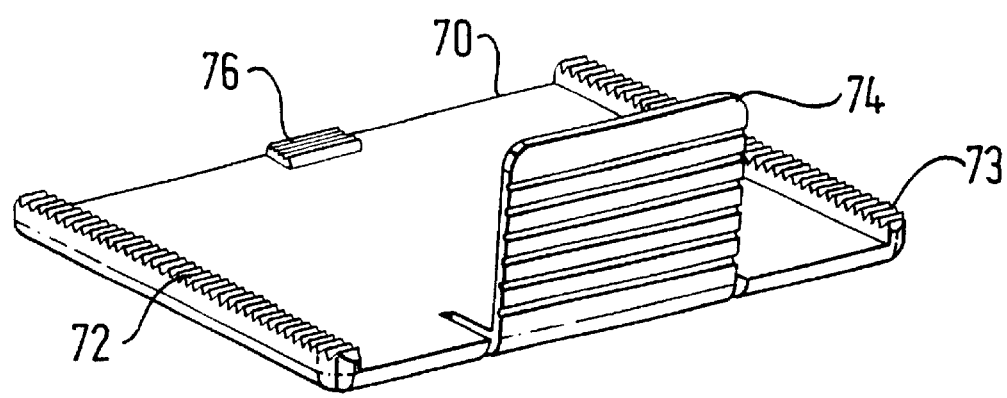
FIG. 4b is a simplified plan view of the mouthpiece slider of the inhalation device of FIG. 3.

The main body 80 may be seen to be shaped for receipt of the cassette and cartridge disc 10 contained therein. Referring to FIG. 4b, the main body includes a drive system for driving the rotation of the disc 10 within the cartridge. The drive system comprises an indexing screw 84 which communicates with the teeth 11 on the circumference of the disc 10 and with drive shaft 86. A fixed wheel 88 is provided to the central portion of the drive shaft 86. Rotation of the disc may be seen to be achievable by a user driven (e.g. by a thumb movement) rotation of the fixed wheel 88 and drive shaft 86 which causes rotation of the indexing screw 84 and hence rotation of the disc 10.

The fixed wheel 88 on the drive shaft 86 may also be seen to communicate with raised toothed portion 76 on the mouthpiece slider 70 such that the rotation of the fixed wheel 88 drives the slidable motion of the mouthpiece slider 70 and hence, translation movement of the mouthpiece 60.

Figure 5:
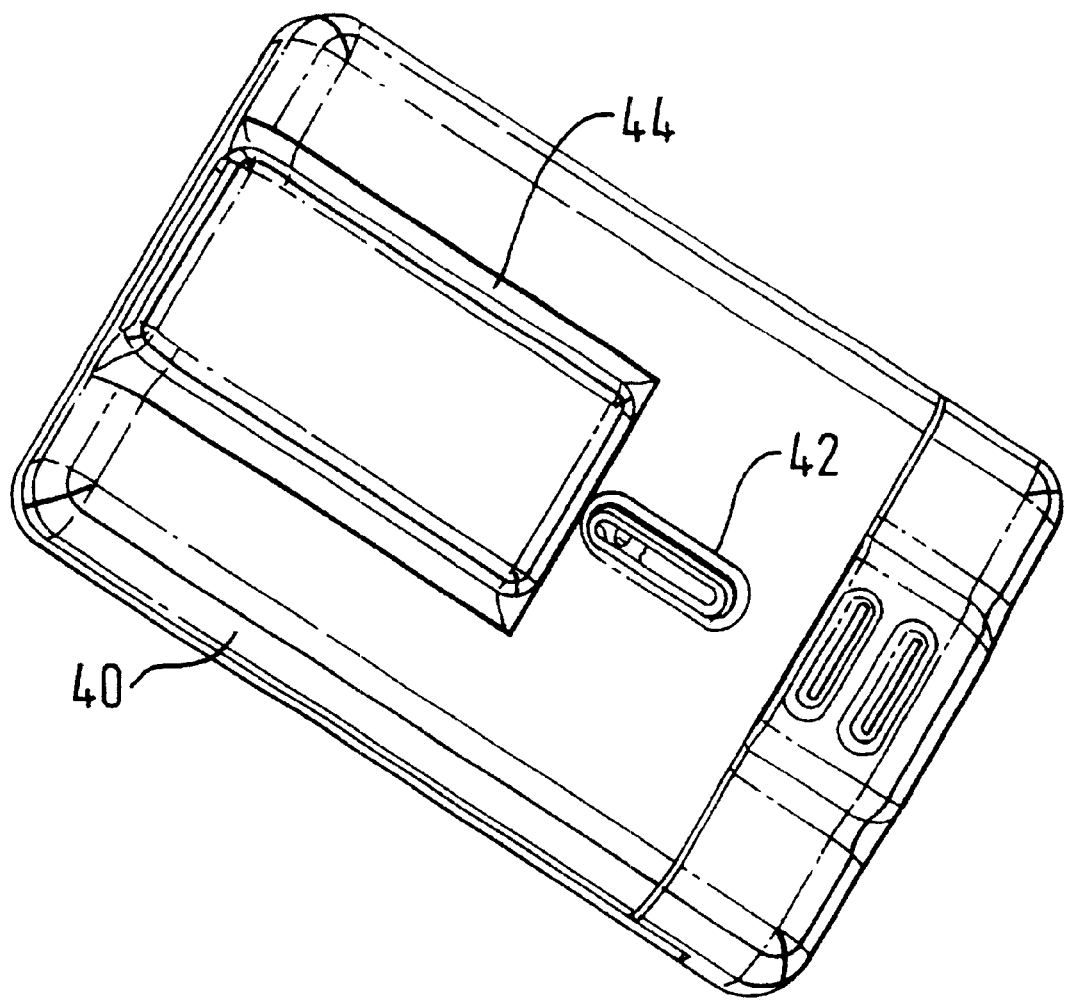
FIG. 5 is a plan view of the inhalation device of FIG. 3 in assembled form.

FIG. 5 shows a view of the inhalation device of FIG. 3 in assembled form with the mouthpiece 60 in the storage position. It may be seen that the window 42 enables the user to view the position of the disc 10 and hence to gain information about the number of doses remaining.

It will be appreciated that variations of the cartridge, cassette and inhalation device of FIGS. 1a to 5 are possible. In particular, variations involving more than two concentric circles of medicament retainers are envisaged. Other drive systems for driving the rotation of the disc may also be envisaged. The drive systems may be driven directly by the user or by electrically powered means. Inhalation devices having a fixed mouthpiece are envisaged.

In one variation (not shown) the tracking groove 17 in the reverse face 16 of the disc 10 is provided with indentations spaced at positions aligned with the positions of the medicament retaining cavities 14 on the top face 12 of the disc 10. The so-indented tracking groove 17 can thus function as a rack which may be driven by a suitably configured pinion drive to achieve the rotation of the disc 10.

Figure 6:
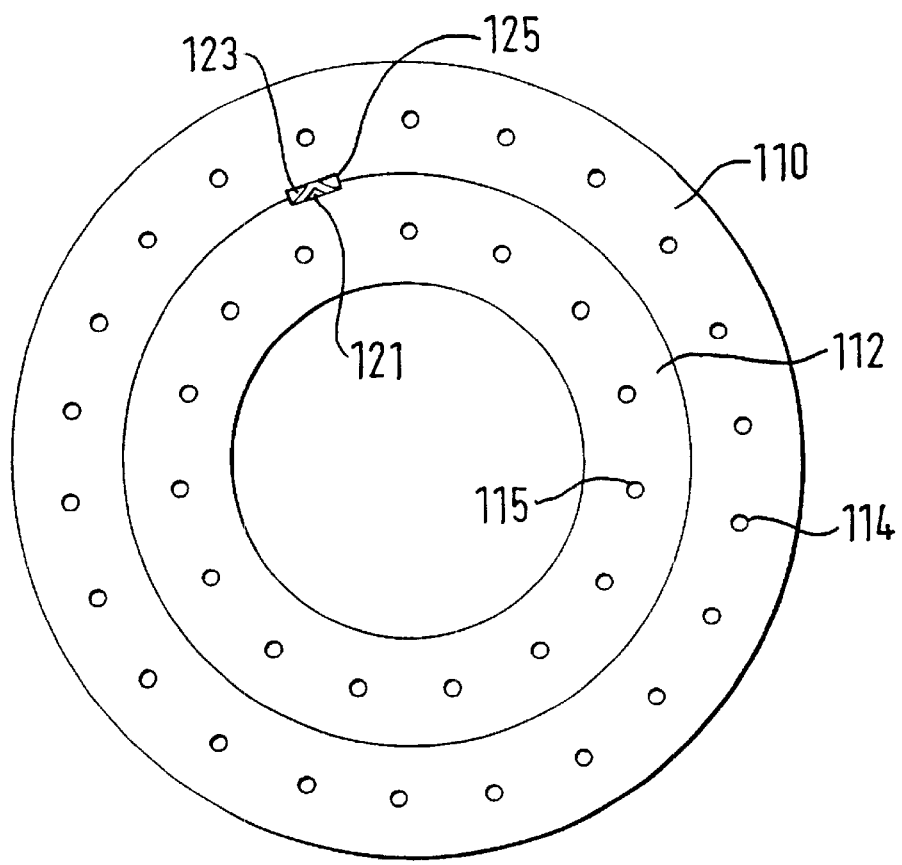
FIG. 6 is a view of the top of a second medicament cartridge in accord with the present invention.

FIG. 6 shows a second medicament cartridge herein comprising outer 110 and inner 112 concentric rings. Each ring is planar and has a top surface having a plurality of medicament retaining cavities 114, 115 in a circular arrangement therein. The outer 114 and inner 115 circles are concentric. The rings 110, 112 are in general, freely rotatable with respect to each other but are also provided with a locking mechanism which is shown in more detail in FIGS. 7a and 7b. The locking mechanism comprises a recessed portion 121 in the outer circumference of the inner ring 112 and flexible fingers 123 in a recessed portion 125 of the inner circumference of the outer ring 110. When the rings 110, 112 are rotated such that the recessed portion 121 of the inner ring 112 is brought into register with the recessed portion 125 of the outer ring 110 it may be seen that the flexible fingers 123 flex into the recessed portion 121 of the inner ring 112 thereby locking the rings 110,112 together.

Figure 7A:
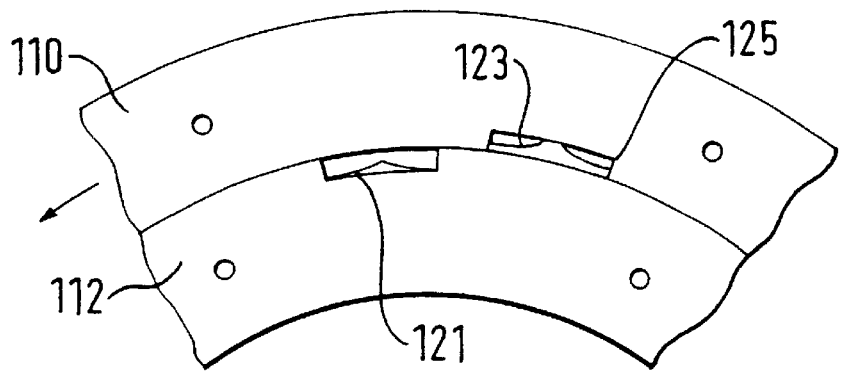
FIG. 7a is a view of a detail of a locking mechanism of the second medicament cartridge of FIG. 6 in the unlocked position.
Figure 7B:
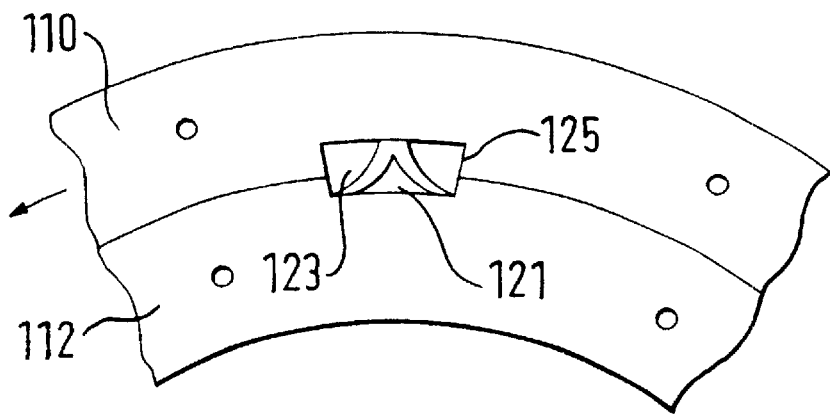
FIG. 7b is a view of a detail of a locking mechanism of the second medicament cartridge of FIG. 6 in the locked position.
Figure 8:
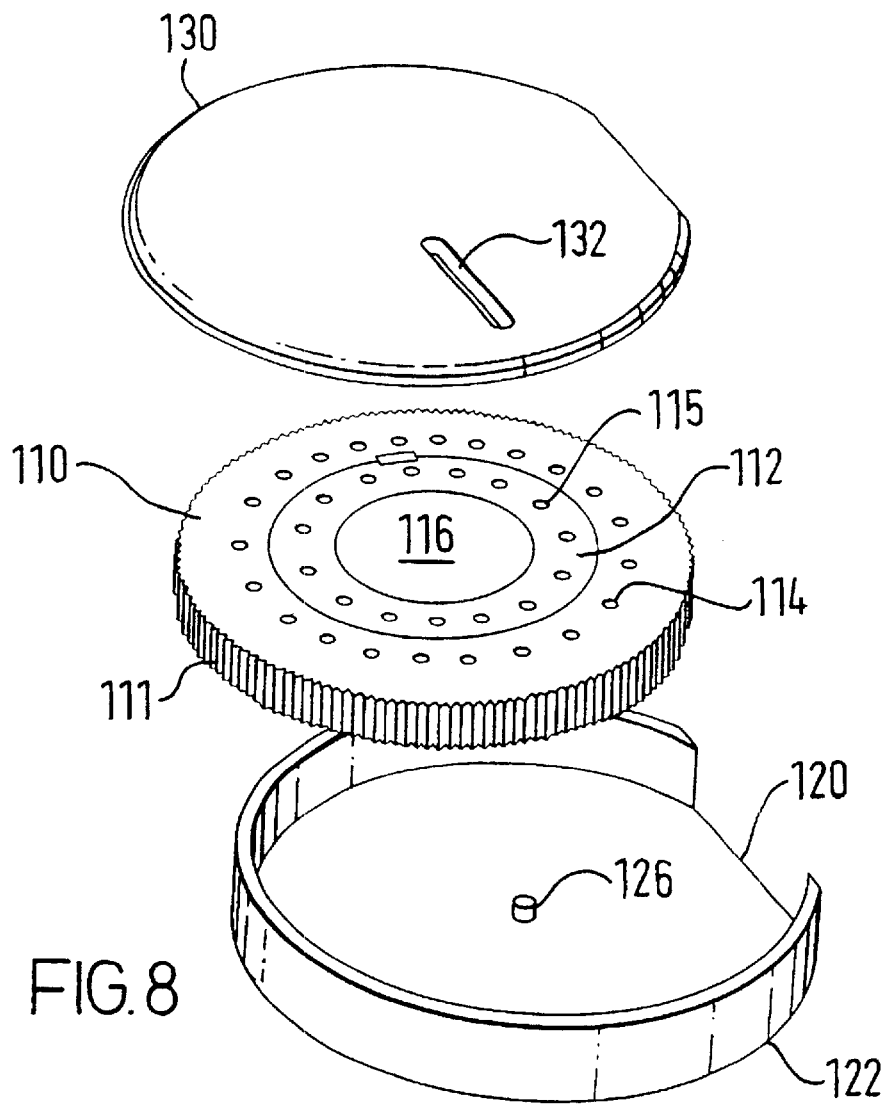
FIG. 8 is an exploded view of a cassette incorporating the medicament cartridge of FIG. 6.

FIG. 8 shows an exploded view of a cassette incorporating the second medicament cartridge of FIGS. 6, 7a and 7b. The cassette has a bottom cover 120 having peripheral walls 122 extending partially therearound. The bottom cover 120 is provided with a mounting peg 126 for receipt of central mounting disc 116. When the cassette is in assembled form, the central mounting disc 116 is snugly received by the inner ring 112 and forms a spindle about which the rings 110, 112 are rotatable. The top cover 130 of the cassette is provided with an exit slit 132 located to register with successive medicament retaining cavities 114, 115 on the top faces of the rings 110, 112. When the cassette is loaded into an inhalation device the exit slit 132 communicates with a mouthpiece (not shown). The outer edge 111 of the outer ring 110 is provided with teeth which are engagable with suitable rotational drive systems. In one aspect, the rotational drive system is identical to that shown in FIG. 4a.

In an inhalation device, the rings 110, 112 are initially positioned relative to each other such that the recessed portion 121 of the inner ring 110 is close to but not in register with the recessed portion 125 of the outer ring. In this initial position the rings 110, 112 are not locked and are thus freely rotable relative to each other. The initial position is shown in FIG. 7a. In the initial position, none of the medicament retainers 114, 115 will be in register with the exit slit 132 of the cassette.

To enable access to a first dose, the outer ring 110 is rotated in the direction which takes the recessed portion 121 of the inner ring 110 further out of register with the recessed portion 125 of the outer ring (anti-clockwise direction, as shown in FIG. 7a) and until a first medicament retainer 114 on the outer ring 110 is brought into register with the exit slit 132. Further rotation of the outer ring 110 in the same direction brings each successive medicament-retaining cavity 114 thereon into registration with the exit slit 132.

Still further rotation brings the recessed portion 125 of the outer ring 110 into register with the recessed portion 121 of the inner ring 110 such that the locking mechanism flexes into the locked position (shown in FIG. 7b). Further rotation of the outer ring 110 causes rotation of the inner ring 112 which thus, enables the medicament retainers 115 thereon to be brought successively into register with the exit slit 132. In this way, medicament may be successively accessed from both the outer 110 and inner 112 rings.

Figure 9:
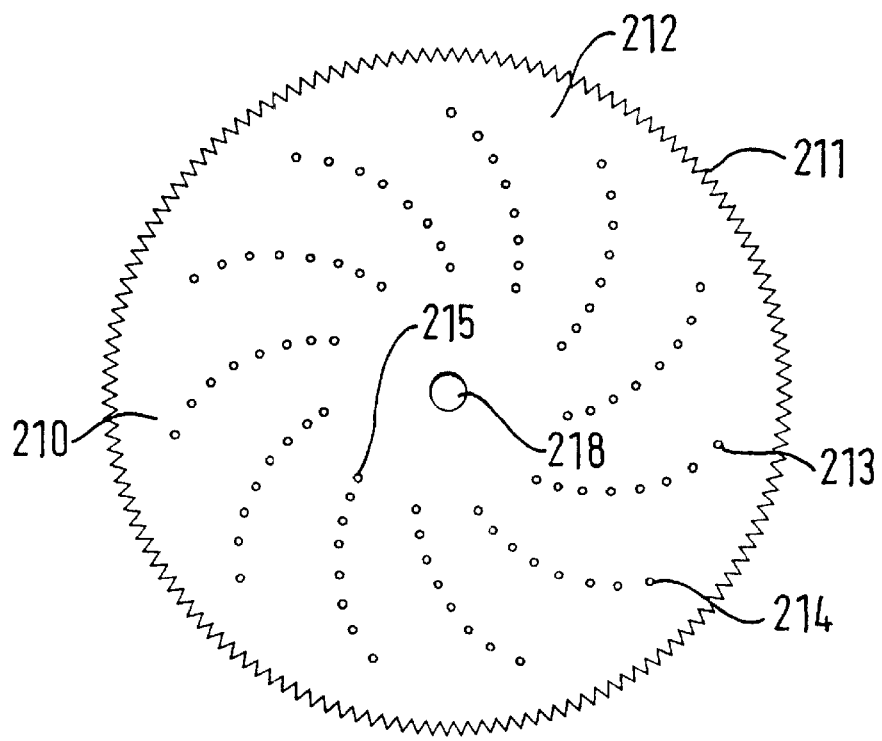
FIG. 9 is a top view of an alternative embodiment of a medicament cartridge in accord with the present invention.

FIG. 9 shows a medicament cartridge in the form of a rigid disc 210 having teeth 211 on the circumference thereof. The top face of the disc 212 is provided with a plurality of medicament retaining pockets 213–215 arranged in a spiral ray arrangement. As can be seen, the pockets on the different spiral rays (e.g. 213, 214) form concentric circles with respect to hole 218, which is centrally located to enable the disc to be mounted for rotation.

Figure 10A:
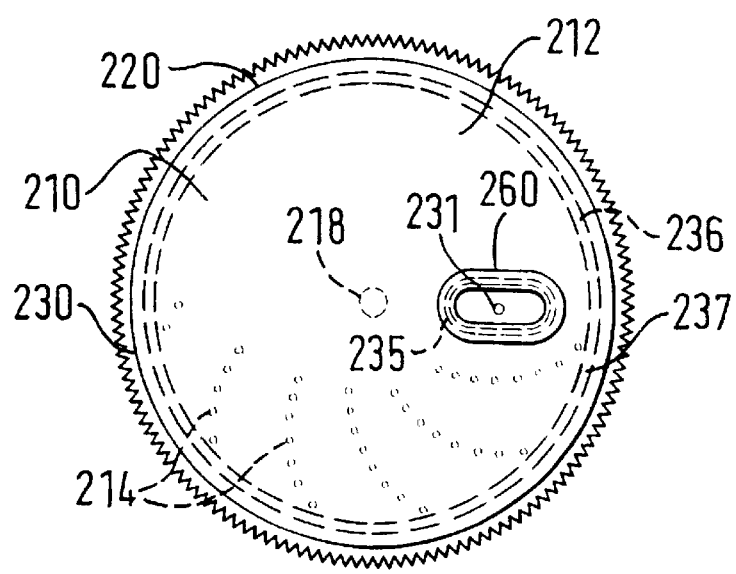
FIG. 10a is a top view of a cassette incorporating the medicament cartridge of FIG. 9.

FIG. 10a shows a top view of a cassette incorporating a medicament cartridge 210 of FIG. 9. The top face of the cartridge 212 is provided with a plurality of medicament retaining pockets 214 arranged in a spiral ray arrangement (individual pockets on different rays forming concentric circles with respect to the centre of the disc 218). In operation, cartridge 210 is rotated relative to top and bottom covers 230 and 220 to move successive medicament retaining pockets 214 into position within mouthpiece 260. The pockets 214 are arranged such that on rotation of disc 210 each pocket 214 is successively moved into position 231 within mouthpiece 260 over the air inlet (not shown). Gasket 235 forms a seal between the base of the mouthpiece housing and the medicament cartridge 210. Further seals between the top 230 and bottom 220 covers with cartridge 210 are formed with gaskets 236 and 237 respectively.

Figure 10B:
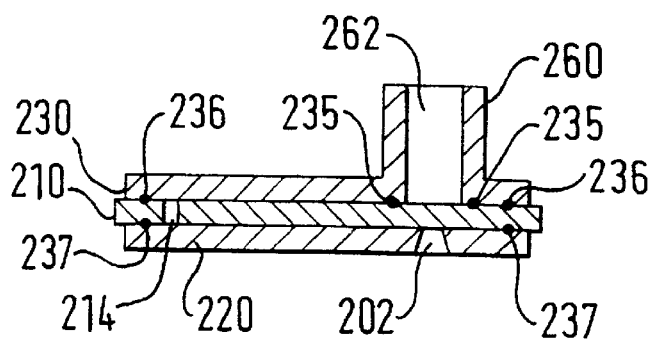
Figure 10C:
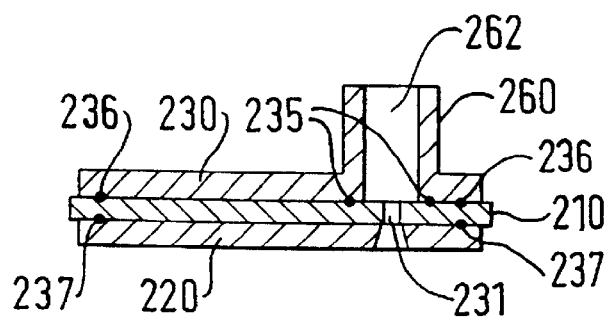

A side perspective of the cassette shown in FIG. 10a is given in FIGS. 10b and 10c. The cassette is in the 'sealed position' in FIG. 10b, there being no medicament retaining pocket 214 in position below mouthpiece 260 such that air inlet 202 is not in communication with air outlet 262. In operation (shown in FIG. 10c) cartridge 210 is rotated to move pocket 214 into position 231 such that it is in communication with air inlet 202 and air outlet 262; on inhalation by the patient, medicament within pocket 231 is aspirated through mouthpiece 260 to the patient.

Figure 10D:
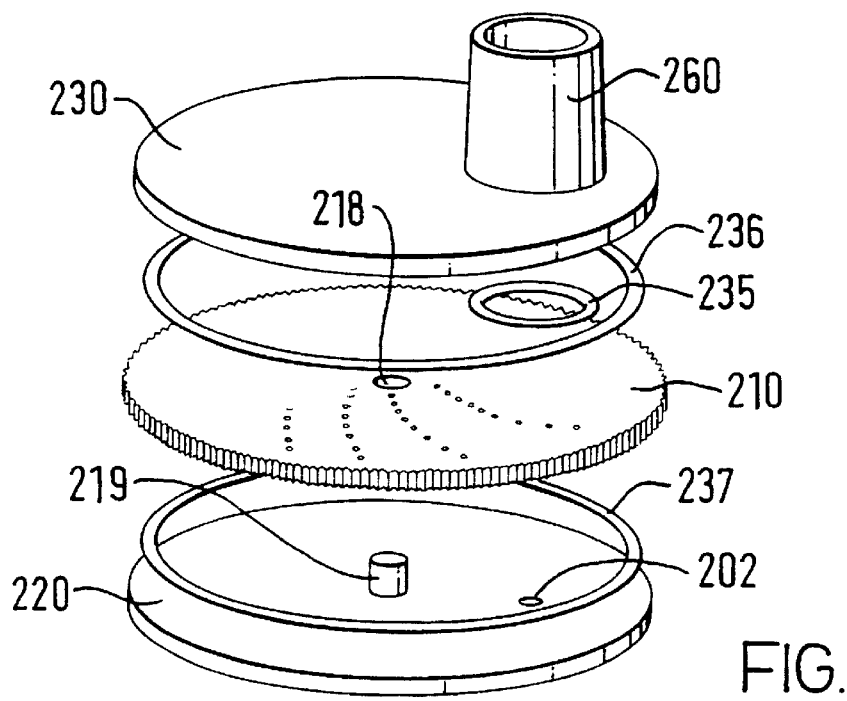

An exploded view of the cassette depicted in FIGS. 10a–c is shown in FIG. 10d. The cassette consists of top cover 230 bearing mouthpiece 260 and air outlet (not shown). Bottom cover 220 is provided with air inlet 202 and central peg 219 to enable cartridge 210 to be mounted for rotation on central hole 218. Gaskets 236 and 237 seal cartridge 210 between top 230 and bottom 220 covers, while gasket 235 seals cartridge 210 from air inlet 202 when the cassette is assembled.

The medicament cartridge and inhalation device herein is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (-)-4-amino-3, 5-dichloro-α-[[[6-[2-(2-pyridinyl) ethoxy] hexyl] methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti inflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. Medicament cartridge for use in an inhalation device comprising a carrier having a plurality of medicament retainers in a concentric circular path arrangement, wherein each concentric circular path is independently rotatable relative to and is lockably engageable to an adjacent ring thereto.

2. Medicament cartridge according to claim 1, wherein said carrier is substantially planar.

3. Medicament cartridge according to claim 2, wherein said carrier is substantially rigid.

4. Medicament cartridge according to claim 3, wherein said carrier is circular in shape and is rotationally mountable.

5. Medicament cartridge according to claim 4, wherein said carrier comprises plural concentric rings, each ring comprising a plurality of medicament retainers in a circular path arrangement.

6. Medicament cartridge according to claim 1, wherein said medicament retainers further define a spiral ray arrangement.

7. Medicament cartridge according to claim 1, wherein each medicament retainer comprises a pocket.

8. Medicament cartridge according to claim 1, wherein a seal is provided to each pocket.

9. Medicament cartridge according to claim 8, wherein said seal comprises a sealing tape arranged along each circular path and wherein each cavity is accessible by progressive removal of the tape.

10. Medicament cartridge according to claim 8, wherein said seal comprises a rubber seal.

11. Medicament cartridge according to claim 1, wherein each medicament retainer comprises a hole in the carrier.

12. Medicament cartridge according to claim 11, wherein each hole is provided with a mesh for retention of medicament.

13. Medicament cartridge according to claim 12, wherein the medicament is applied to the mesh by a wet or dry printing method.

14. Medicament cartridge according to claim 1, wherein each medicament retainer is sized to retain a single dose of medicament.

15. Medicament cartridge according to claim 1, having from 30 to 500, preferably from 100 to 300, medicament retainers.

16. Medicament cartridge according to claim 1, wherein medicament is present in one or more of the medicament retainers.

17. Inhalation device comprising
a housing having an air inlet, an air outlet and an airway therebetween;
a medicament carrier having a plurality of medicament retainers in a concentric circular path arrangement; and
a mover for moving the medicament carrier relative to the housing so as to bring successive medicament retainers individually into communication with the airway.

18. Inhalation device according to claim 17, wherein said medicament retainers further define a spiral ray arrangement.

19. Inhalation device according to claim 17, wherein said medicament carrier is a substantially rigid circular disc which is rotatable relative to the housing.

20. Inhalation device according to claim 19, wherein the circumference of said disc is provided with teeth and said teeth engage a worm drive for drivable rotation of said disc.

21. Inhalation device according to claim 19, wherein each medicament retainer comprises a pocket in a first face of the disc.

22. Inhalation device according to claim 17, wherein each medicament retainer has a seal.

23. Inhalation device according to claim 22, wherein each medicament retainer is individually unsealable.

24. Inhalation device according to claim 23, wherein said seal is provided by a gasket and the interior surfaces of said housing.

25. Inhalation device according to claim 24, wherein a first gasket is positioned between the base of the air outlet and the surface of the upper face of the disc, a second gasket is positioned between the circumference of the upper face of the disc and the housing, and a third gasket is positioned between the circumference of the lower face of the disc and the housing.

26. Inhalation device according to claim 24, wherein any gasket comprises an organic polymeric material.

27. Inhalation device according to claim 26, wherein said polymeric material is selected from the group consisting of rubber, neoprene, polyester, polyethylene, polycarbonate, polyacetal, polytetra-fluroethylene and nylon.

28. Inhalation device according to claim 17, wherein said air outlet is in communication with a mouthpiece.

29. Inhalation device comprising
a housing having an air inlet, an air outlet and an airway therebetween;
a medicament carrier having a plurality of medicament retainers in a concentric circular path arrangement, each medicament retainer having a seal;
a mover for moving the medicament carrier relative to the housing so as to bring successive medicament retainers individually into communication with the airway; and
an actuator for progressively unsealing each medicament retainer.

30. Inhalation device according to claim 29, wherein said medicament retainers further define a spiral ray arrangement.

31. Inhalation device according to claim 29, wherein each medicament retainer comprises a pocket.

32. Inhalation device according to claim 31, wherein said seal comprises a sealing tape arranged along each circular path and wherein each pocket is serially accessible by peelable removal of the tape.

33. Inhalation device according to claim 32, wherein an end of said sealing tape connects to said actuator and peelable removal of the sealing tape is achievable by movement of the actuator.

34. Inhalation device according to claim 33, wherein said actuator is rotatable relative to the housing such that rotation of the actuator results in coiling of the tape around the actuator.

35. Inhalation device according to claim 34, wherein the actuator is an axially mounted tapered pole.

36. Inhalation device according to claim 29, wherein said actuator comprises a piercer for piercably unsealing a medicament retainer.

37. Inhalation device according to claim 29, wherein said air outlet is in communication with a mouthpiece.

38. Use of an inhalation device according to claim 17 for the administration of medicament to a patient.

39. Use of an inhalation device according to claim 29 for the administration of medicament to a patient.

\* \* \* \* \*